US012605698B2

(12) United States Patent
Marbaix et al.

(10) Patent No.: US 12,605,698 B2
(45) Date of Patent: Apr. 21, 2026

(54) CATALYTIC ASSEMBLY COMPRISING A MICROMETRIC FERROMAGNETIC MATERIAL AND USE OF SAID ASSEMBLY FOR HETEROGENEOUS CATALYSIS REACTIONS

(71) Applicants: CENTRE NATIONAL DE LA RECHERCHE SCIENTIFIQUE, Paris (FR); INSTITUT NATIONAL DES SCIENCES APPLIQUEES DE TOULOUSE, Toulouse (FR)

(72) Inventors: Julien Marbaix, Bordeaux (FR); Sumeet Kale, Pune (IN); Stéphane Faure, Launaguet (FR); Aikaterini Soulantika, Clermont le Fort (FR); Bruno Chaudret, Vigoulet Auzil (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 1048 days.

(21) Appl. No.: 17/761,181

(22) PCT Filed: Sep. 18, 2020

(86) PCT No.: PCT/FR2020/051626
§ 371 (c)(1),
(2) Date: Mar. 16, 2022

(87) PCT Pub. No.: WO2021/053307
PCT Pub. Date: Mar. 25, 2021

(65) Prior Publication Data

US 2023/0241588 A1 Aug. 3, 2023

(30) Foreign Application Priority Data

Sep. 19, 2019 (FR) ...................................... 1910344

(51) Int. Cl.
*B01J 23/755* (2006.01)
*B01J 21/12* (2006.01)
(Continued)

(52) U.S. Cl.
CPC ............. *B01J 23/755* (2013.01); *B01J 21/12* (2013.01); *B01J 23/10* (2013.01); *B01J 23/745* (2013.01);
(Continued)

(58) Field of Classification Search
CPC . B01J 23/755; B01J 21/12; B01J 23/10; B01J 23/745; B01J 35/33; B01J 35/40;
(Continued)

(56) References Cited

U.S. PATENT DOCUMENTS 4,359,379 A 11/1982 Ushio et al.
5,645,808 A * 7/1997 Krause ............... B01D 53/8668 423/245.3
(Continued)

FOREIGN PATENT DOCUMENTS

JP 2013-248610 12/2013
JP 2015-187105 A 10/2015
(Continued)

OTHER PUBLICATIONS

International Search Report dated Jan. 29, 2021.
Japanese Office Action dated Oct. 4, 2024.
Chinese Office Action dated Aug. 14, 2023.

*Primary Examiner* — Prem C Singh
*Assistant Examiner* — Francis C Campanell
(74) *Attorney, Agent, or Firm* — IPSILON USA, LLP

(57) ABSTRACT

The invention relates to a catalytic assembly for carrying out a heterogeneous catalysis reaction in a given temperature range T, characterized in that it comprises the association of at least one catalytic compound capable of catalyzing said
(Continued)

reaction in the temperature range T and of a ferromagnetic material in the form of micrometric particles and/or wires, said ferromagnetic material being capable of being heated by magnetic induction by means of a field inductor. The invention also relates to the use of said catalytic assembly for implementing a heterogeneous catalysis reaction such as a methanation reaction.

20 Claims, 6 Drawing Sheets

(51) Int. Cl.

| | |
|---|---|
| ***B01J 23/10*** | (2006.01) |
| ***B01J 23/745*** | (2006.01) |
| ***B01J 35/33*** | (2024.01) |
| ***B01J 35/40*** | (2024.01) |
| ***B01J 35/55*** | (2024.01) |
| ***B01J 35/58*** | (2024.01) |
| ***C07C 1/12*** | (2006.01) |

(52) U.S. Cl.
CPC ............... *B01J 35/33* (2024.01); *B01J 35/40* (2024.01); *B01J 35/55* (2024.01); *B01J 35/58* (2024.01); *C07C 1/12* (2013.01); *B01J 2235/00* (2024.01); *B01J 2235/30* (2024.01); *C07C 2521/12* (2013.01); *C07C 2523/10* (2013.01); *C07C 2523/755* (2013.01)

(58) Field of Classification Search
CPC ........ B01J 35/50; B01J 35/58; B01J 2235/00; B01J 2235/30; B01J 35/55; B01J 37/04; B01J 37/342; B01J 23/83; C07C 1/12; C07C 2521/12; C07C 2523/10; C07C 2523/755; C10G 2/50
USPC .......................................................... 208/124
See application file for complete search history.

(56) References Cited

U.S. PATENT DOCUMENTS

| | | | | |
|---|---|---|---|---|
| 2017/0106353 | A1 | 4/2017 | Lipiec et al. | |
| 2017/0348454 | A1 * | 12/2017 | Sun .......................... | B01J 37/04 |
| 2018/0244592 | A1 | 8/2018 | Hojlund Nielsen | |
| 2019/0144376 | A1 | 5/2019 | Hojlund Nielsen | |
| 2020/0047166 | A1 | 2/2020 | Bordet et al. | |

FOREIGN PATENT DOCUMENTS

| | | |
|---|---|---|
| JP | 2018-507007 A | 3/2018 |
| WO | 2016/102567 | 12/2015 |

* cited by examiner

CATALYTIC ASSEMBLY COMPRISING A MICROMETRIC FERROMAGNETIC MATERIAL AND USE OF SAID ASSEMBLY FOR HETEROGENEOUS CATALYSIS REACTIONS

RELATED APPLICATION

This application is a National Phase of PCT/FR2020/051626 filed on Sep. 18, 2020, which claims the benefit of priority from French Patent Application No. 19 10344, filed on Sep. 19, 2019, the entirety of which are incorporated by reference.

FIELD OF THE INVENTION

The present invention relates the field of heterogeneous catalysis, notably a catalytic assembly for carrying out a gas-solid heterogeneous catalysis reaction and to the use thereof for such catalysis reactions, in particular for hydrocarbon synthesis reactions.

Gas-solid heterogeneous catalysis reactions comprise contacting at least one gaseous reactant with a catalytic solid compound. These catalysis processes require a step of heating, sometimes at high temperature, for the implementation of the reaction, and are therefore expensive and highly energy-consuming. Research has therefore focused on more economical solutions and notably on reactions that are less energy intensive.

PRIOR ART

Among these solutions, international application WO 2014/162099 has proposed a heterogeneous catalysis process in which the heating is carried out by magnetic induction in order to reach the temperature necessary for the reaction. More particularly in this process, the reactant is contacted with a catalytic composition which comprises a ferromagnetic nanoparticulate component, the surface of which consists at least partially of a compound that is a catalyst for said reaction, said nanoparticulate component being heated by magnetic induction in order to reach the desired temperature range. This heating may be carried out by means of a field inductor external to the reactor. In this system, the nanoparticles are heated by their own magnetic moment, enabling the heating of the catalyst and the startup of the catalytic reaction. The heating is therefore initiated within the very heart of the reactor, rapidly with minimal energy input. This results in substantial savings.

However, these ferromagnetic nanoparticles require a high heating power: for example of between 1100 and 2100 W/g at 100 kHz for FeC nanoparticles (recent publication by Kale et al., *Iron carbide or iron carbide/cobalt nanoparticles for magnetically-induced CO2 hydrogenation over Ni/SiRAlOx catalysts*, Catal. Sci. Technol., 2019, 9, 2601.

Furthermore, document WO 2014/162099 stresses the optimization of the size of the nanometric particles and suggests a size of the ferromagnetic nanoparticulate component of between 5 nm and 50 nm with an optimal size of 20 nm in the case of iron.

It therefore turns out that the cost of these reactions remains high, due in particular to the heating power required and the cost of the catalytic particles in nanometric form, notably the magnetic nanoparticles.

Furthermore, the nanometric size of these materials involves, in general, handling precautions.

Another problem linked to the use of nanoparticles is the modification of their heating properties due, on the one hand, to their tendency toward sintering during high-temperature reactions, and, on the other hand, to aging resulting from a change in the chemical order in said nanoparticles (modification of the structure and of the local chemical composition).

Objectives of the Invention

A first objective of the invention is therefore to overcome the aforementioned drawbacks by proposing a catalytic component that makes it possible to further reduce the cost of these heterogeneous catalysis reactions, while maintaining the reaction performance thereof.

Another objective of the invention is to propose a catalytic component that makes it possible to reduce the proportion of the nanometric particles in the reactor.

Another objective of the invention is to propose a catalytic component that enables a maintaining of the heating properties and of the catalytic properties over very long periods of time, while being suitable for intermittent operation.

DESCRIPTION OF THE INVENTION

In the search for new savings, the inventors discovered, surprisingly, that the heating agents may not necessarily be in nanometric form, but may be present in the reactor in the form of micrometric powder or wires of micrometric diameter.

For this purpose, the present invention proposes a catalytic assembly for carrying out a heterogeneous catalysis reaction in a given temperature range T, said catalytic assembly being characterized in that it comprises the combination:

- of at least one catalytic compound formed of metallic particles and capable of catalyzing said reaction in the temperature range T
- and of at least one ferromagnetic material in the form of micrometric particles having a particle size of between 1 μm and 1000 μm and/or of wires based on iron or on an iron alloy having a wire diameter of between 1 μm and 1 mm, said ferromagnetic material being capable of being heated by magnetic induction by means of a field inductor.

The examples presented later on in the text show a good energy efficiency of such a micrometric ferromagnetic material as a heating agent. In particular, the results obtained with such a heating agent which is no longer nanometric, but of much greater size, are equivalent to those obtained in the process of WO 2014/162099.

According to a first embodiment of the invention, the catalytic assembly is in the form of a powder comprising a mixture of at least one catalytic compound in particulate form with micrometric particles of the ferromagnetic material.

As regards the micrometric particles of the ferromagnetic material, they advantageously have a particle size of between 1 μm and 100 μm, preferably between 1 μm and 50 μm, more preferably between 1 μm and 10 μm, that is to say a size much greater than those of the nanoparticles described in document WO 2014/162099.

With such micrometric ferromagnetic particles, which admittedly sometimes have a tendency toward agglomeration, no sintering is observed and the effectiveness of the heating is thus maintained.

Said catalytic compound may in particular be formed of metallic particles (metal, metal oxide or a combination of the two) of catalyst which are positioned at the surface of an oxide forming a support for the catalyst, such as an oxide of the following elements: silicon, aluminum, titanium, zirconium, cerium, constituting a catalyst-oxide compound.

The oxide support for the catalyst may be for example $Al_2O_3$, $SiO_2$, $TiO_2$, $ZrO_2$, $CeO_2$ constituting a catalyst-oxide compound that is in the form of a powder of micrometric or nanometric size which is mixed with the ferromagnetic material in the form of micrometric powder. The mixture of these powders (catalyst-oxide compound with the microparticulate ferromagnetic material) thus creates intimate contact between the heating agent and the catalyst, making it possible to rapidly start the catalysis reaction at the surface of the catalyst.

According to a second embodiment of the catalytic assembly of the present invention, the catalytic compound comprises metallic particles (in form of metal, metal oxide or a combination of the two) of catalyst which are positioned at the surface of the ferromagnetic material that is in the form of wires.

Advantageously, the ferromagnetic material that is in the form of wires comprises steel wool containing wires based on iron or on an iron alloy, having a wire diameter of between 10 micrometers and 1 millimeter, preferably between 20 μm and 500 μm, more preferably between 50 μm and 200 μm.

The ferromagnetic material is advantageously based on iron, or on an iron alloy, comprising at least 50 wt % iron, preferably comprising at least 80 wt % iron.

The ferromagnetic material may notably be composed of superfine steel wool, forming an entanglement of wires composed of at least 90 wt % iron, and of which the diameter of the wires may be between 50 μm and 100 μm.

The metallic catalyst particles of the catalytic compound may be chosen from manganese, iron, nickel, cobalt, copper, zinc, ruthenium, rhodium, palladium, iridium, platinum, tin, or an alloy comprising one or more of these metals. Preferentially, the metallic catalyst particles of the catalytic compound are nickel or ruthenium particles.

The present invention also relates to the use of the catalytic assembly described above for the implementation of a heterogeneous catalysis reaction comprising the contacting, in a reactor, of at least one reactant with said catalytic assembly and the heating of said ferromagnetic material by magnetic induction by means of a field inductor external to the reactor, so as to catalyze said reaction in the temperature range T.

Quite surprisingly, steel wool, a cheap and readily available material that can be purchased in home improvement stores, has proved to be an excellent heating agent. More particularly, very fine (superfine) steel wool, having a wire diameter of less than a millimeter, is effective for enabling the heating of said catalyst by magnetic induction and may also be a good catalyst support.

This material is very easy to use and has a very long service life. Furthermore, it is easily recyclable and is non-polluting.

The heterogeneous catalysis reaction is advantageously a hydrocarbon synthesis reaction, more particularly the heterogeneous catalysis reaction is a hydrogenation reaction of a carbon oxide in the gaseous state, such as a methanation reaction starting from carbon dioxide and dihydrogen.

BRIEF DESCRIPTION OF THE DRAWINGS

The invention will be clearly understood on reading the following description of non-limiting exemplary embodiments with reference to the appended drawings in which.

EXAMPLES

Example 1: Preparation of the Catalyst

Figure 1A:
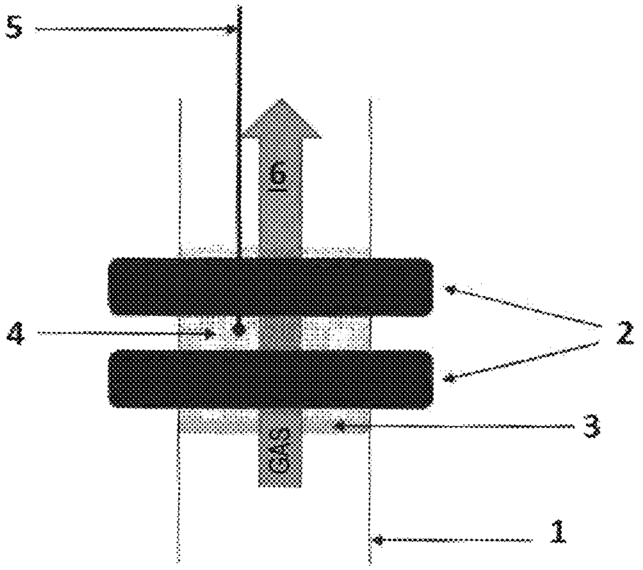
FIG. 1A is a simplified partial diagram of a reactor for the use of a catalytic assembly according to the invention for a gas-solid heterogeneous catalysis reaction according to the invention, under an upward gas flow, showing the positioning of the catalyst+heating agent assembly in the part of the tubular reactor encircled by the external magnetic field inductor.

Preparation of the catalyst on cerium oxide support Nickel at 10 wt % on cerium oxide (abbreviated to Ni(10 wt %)/$CeO_2$) is prepared by decomposition of $Ni(COD)_2$ in the presence of $CeO_2$ in mesitylene.

According to a conventional preparation process, 1560 mg of $Ni(COD)_2$ are dissolved in 20 mL of mesitylene then 3 g of $CeO_2$ are added. The mixture obtained is heated at 150° C. under an argon atmosphere for 1 hour with vigorous stirring. This mixture, initially milky white, is black at the end of the reaction. After decantation, the translucent supernatant is removed and the particles obtained are washed three times with 10 mL of toluene. The toluene is then removed under vacuum, making it possible to obtain a thick powder of Ni10 wt %/$CeO_2$ (3.5 g) which is collected and stored in a glove box. Analysis by inductively coupled plasma mass spectrometry (ICP-MS) confirms the loading of 9 wt % of nickel (10% targeted) of the cerium oxide. Observation by transmission electron microscopy (TEM) and EDS analysis show the presence of small monodisperse particles of nickel (with the size of 2-4 nm).

Process for Preparing Ni on SiRAlOx®

In a Fischer-Porter bottle and under an inert atmosphere, 0.261 g of $Ni(COD)_2$ is dissolved in 20 mL of mesitylene and 0.500 g of SiRAlOx® are added. The mixture is heated at 150° C. for one hour with stirring. After returning to ambient temperature, the powder is left to precipitate, then the supernatant is removed and the powder is washed three times with 10 mL of THF. The powder is then dried under vacuum and stored under an inert atmosphere.

Mixture of Iron Powder+$Ni/CeO_2$ 2 g of iron powder are mixed with 1 g of nickel catalyst deposited on cerium oxide prepared previously. Observation with a scanning electron microscope and also EDS mapping make it possible to visualize grains of iron powder having a size of the order of 3-5 μm and to confirm that the nickel is indeed present on the cerium oxide $CeO_2$.

Example 2: Preparation of the Catalyst on Steel Wool Support

Superfine steel wool (Gerlon, purchased from Castorama). ICP-MS analysis of the superfine steel wool gives a composition of 94.7 wt % of iron. EDS mapping shows the presence of numerous impurities on the surface of the wool (mainly potassium, manganese, silicon). SEM observation makes it possible to determine the diameter of the wires of the superfine steel wool used, which is around 100 μm and has a rough and uneven surface.

The experimental protocol for depositing nickel metal on superfine steel wool (entanglement of wires of around 100 μm in diameter, containing 94.7 wt % of iron) is substantially the same as on $CeO_2$. 1560 mg of $Ni(COD)_2$ are dissolved in 100 mL of mesitylene in order to completely submerge the steel wool (3 g). After one hour under rapid stirring at 150° C. under argon, the mixture is placed in a glove box and the solution (of black color) is drained off. The steel wool has itself also turned black. The steel wall is then rinsed with toluene, and then dried under vacuum for 30 minutes and stored in a glove box. Observation by scanning electron microscopy (SEM) and energy-dispersive x-ray spectroscopy show the deposition of polydisperse particles of nickel (100 nm-1000 nm) on the surface of the wires of the steel wool.

ICP-MS analysis over three different zones shows different nickel loadings: 1.23%, 1.44% and 1.33% (weight percentages). These differences between these loadings are quite small, the surface of the wool appears homogeneous. Despite everything, the amount of nickel deposited is below the targeted percentage of 10 wt % of Ni.

Example 3: Methanation Reaction: Measurements of Conversion and Calculation of the Selectivity The methanation reaction

[Chem. 1]

$$CO_2\bullet + \bullet 4\bullet H_2\bullet \longrightarrow \bullet CH_4\bullet + \bullet 2\bullet H_2O\bullet$$

which is a combination of

[Chem. 2]

$$\bullet CO_2 + \bullet H_2\bullet \longleftrightarrow \bullet CO + \bullet H_2O\bullet$$

and of

Figure 1B:
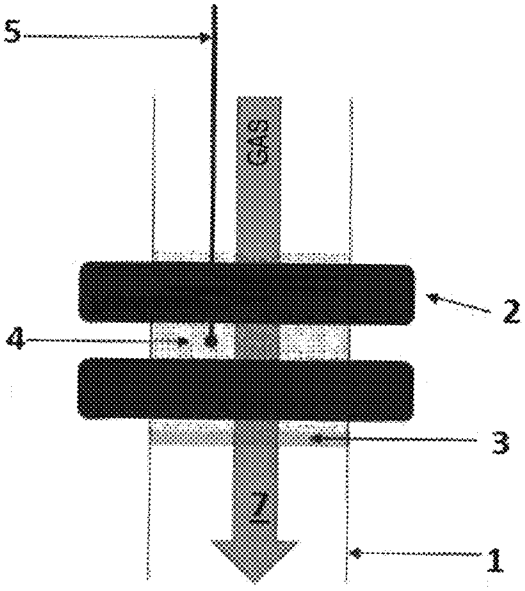
FIG. 1B is a simplified partial diagram of a reactor for the use of a catalytic assembly according to the invention for a gas-solid heterogeneous catalysis reaction according to the invention, under a downward gas flow, showing the positioning of the catalyst+heating agent assembly in the part of the tubular reactor encircled by the external magnetic field inductor.

[Chem. 3]

$$CO\bullet + \bullet 3\bullet H_2\bullet \longrightarrow \bullet CH_4\bullet + \bullet H_2O\bullet$$

is carried out in a quartz fixed-bed tubular continuous reactor 1 (Avitec) (internal diameter: 1 cm with a height of catalyst bed 4, dependent on the heating element, of around 2 cm, resting on sintered glass 3) (cf. FIG. 1); the gaseous stream may be in upward flow 6 (FIG. 1A) or in downward flow 7 (FIG. 1B)). The coil 2 (from the company Five Celes) used is a solenoid with an internal diameter of 40 mm and a height of 40 mm that constitutes the external magnetic field inductor connected to a generator. Its resonance frequency is 300 kHz with a magnetic field varying between 10 and 60 mT. The coil 2 is water cooled.

The measurements of the conversion rates and selectivity as a function of the temperature are carried out with temperature servocontrol of the generator associated with the coil 2. For this purpose, a temperature probe 5 connected to the generator is submerged in the catalyst bed (heating agent+catalyst assembly). The generator sends a magnetic field in order to reach the fixed temperature and then only sends pulses to maintain this temperature. The reaction is carried out at atmospheric pressure and at a temperature that varies between 200° C. and 400° C. The reactor 1 is supplied with $H_2$ and $CO_2$, the flow rate of which is controlled by a flowmeter (Brooks flowmeter) and controlled by Lab View software. The proportions are the following: an overall constant flow rate of 25 mL/min comprises 20 mL/min of $H_2$ and 5 mL/min of $CO_2$. The supplying is carried out at the top of the reactor, the water formed is condensed at the bottom of the reactor (without condenser) and is recovered in a round-bottomed flask. The methane formed and the remaining gases ($CO_2$ and $H_2$) and also the CO are sent to a gas chromatography column (Perkin Elmer, *Clarus* 580 GC column). The conversion of the $CO_2$, the selectivity of the $CH_4$ and the yield of CO and of $CH_4$ are calculated according to the following equations:

[Math. 1]

$$X(CO_2) = CO_2\ \text{conversion} = \frac{(FC(CO)\times A(CO) + FC(CH_4)\times A(CH_4))}{(FC(CO)\times A(CO) + FC(CH_4)\times A(CH_4) + A(CO_2))}$$

$$Y(CO) = CO\ \text{yield} = \frac{(FC(CO)\times A(CO)}{(FC(CO)\times A(CO) + FC(CH_4)\times A(CH_4) + A(CO_2))}$$

$$Y(CH_4) = CH_4\ \text{yield} = \frac{FC(CH_4)\times A(CH_4)}{(FC(CO)\times A(CO) + FC(CH_4)\times A(CH_4) + A(CO_2))}$$

$$S(CH_4) = CH_4\ \text{selectivity} = \frac{FC(CH_4)\times A(CH_4)}{(FC(CO)\times A(CO) + FC(CH_4)\times A(CH_4))}$$

With $FC(CO) = 1.61$ and $FC(CH_4) = 1.71$.

FC is the response factor for each reactant according to reaction monitoring by gas chromatography, A is the area of the peak measured in chromatography.

Measurements of the Energy Efficiency:

Energy efficiency measurements are carried out at the same time as the conversion and selectivity measurements of the methanation reaction. The electricity consumption data for the coil 2 are recovered by means of software developed in the laboratory. The energy efficiency is then calculated according to the following method:

$$\eta_{therm-NRJ} = \frac{Y_{CH4} \cdot D_{m,CH4} \cdot PCS_{CH4}}{D_{m,H2} \cdot PCS_{H2} + E_{bobine}} \quad \text{[Math. 2]}$$

PCS (gross calorific value) represents the amount of energy released by the combustion of 1 mg of gas; the values given by the literature are $PCS_{H2}$=141.9 MJ/kg and $PCS_{CH4}$=55.5 MJ/kg, $Y_{CH4}$ being the $CH_4$ yield of the reaction, $D_{mi}$ being the mass flow rate of the product i, $E_{bobine}$ corresponds to the energy consumed by the inductor in order to operate (namely, to generate the magnetic field and cool the system).

Figure 7:
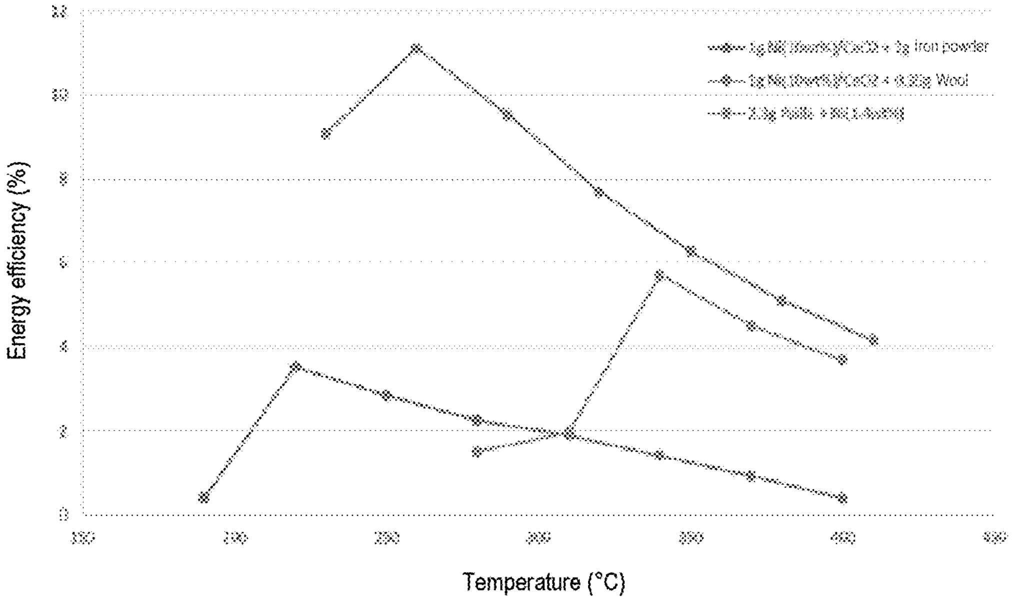
FIG. 7 is a graph comparing the energy efficiency (expressed in %) as a function of temperature for the three types of catalytic assemblies forming catalytic beds tested in the examples presented in FIGS. 4, 5 and 6.

The energy efficiency is expressed in % in FIG. 7.

Example 4: Comparison of Various Ferromagnetic Materials as Heating Agents

Figure 2:
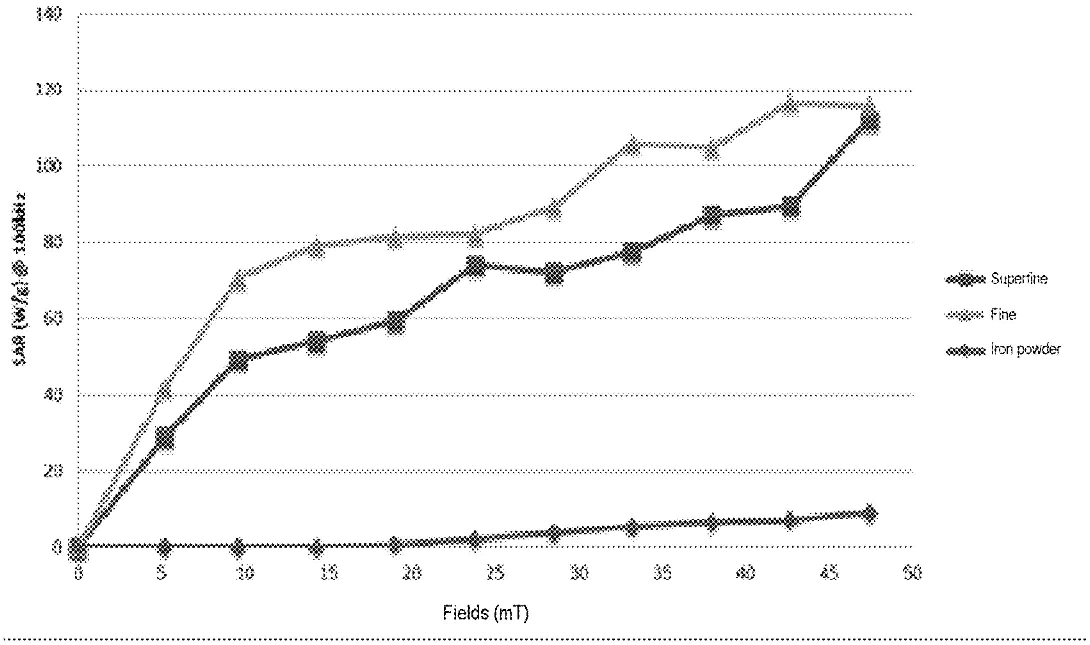
FIG. 2 is a graph comparing the performance of various ferromagnetic materials, carried out under argon at 100 kHz (specific absorption rate (denoted SAR) corresponding to the amount of energy absorbed per unit weight, expressed in watts per gram of material, as a function of the alternating magnetic field intensity applied, expressed in mT): iron powder having microparticles with the size of the order of 3-5 μm, fine steel wool (wire diameter of greater than 1 mm) and superfine steel wool (wire diameter of less than 1 mm, of the order of 100 μm)

Iron powder, fine steel wool and superfine steel wool were compared. The measurements of the specific absorption rate (SAR) (corresponding to the amount of energy absorbed per unit mass, expressed in watts per gram of material), as a function of the alternating magnetic field intensity applied, expressed in mT) were carried out at 100 kHz under argon. The results are grouped together in FIG. 2.

Figure 3:
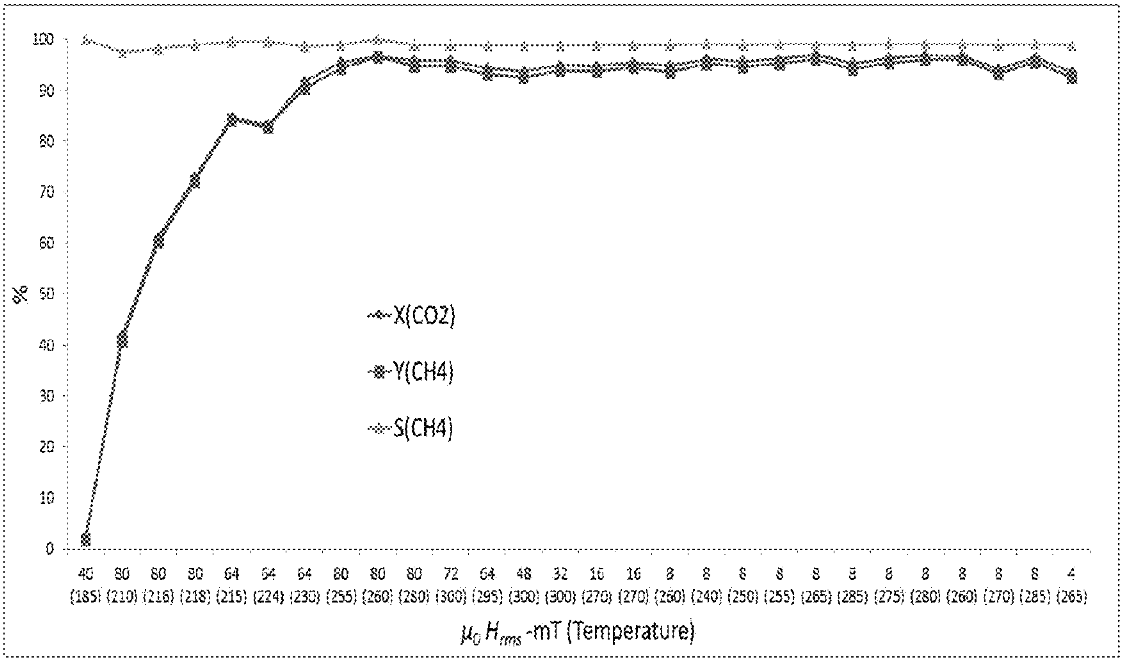
FIG. 3 is a graph presenting results of the use of a catalytic assembly according to the invention for a methanation reaction using iron powder as heating agent and an Ni on SiRAlOx® (silicon aluminum oxide from SESAL) catalyst.

It might then be expected to have to provide the microparticulate iron powder and the steel wool with a higher field than for the nanoparticles. But the results from FIG. 3 show that this is not the case. For the iron carbide nanoparticles, it is necessary to provide a field of around 48 mT to achieve a yield close to 90%. With the iron powder, after launching the reaction, a field of only 8 mT is necessary. The distinctive feature of the iron powder and of the steel wool lies in the eddy currents that come into play and lead to a reduction of the magnetic field for heating the material.

The micrometric iron powder and the micrometric steel wool therefore constitute advantageous ferromagnetic materials for in situ heating, by magnetic induction, of the reactors carrying out gas-solid catalytic reactions such as methanation reactions starting from carbon dioxide and dihydrogen, which is presented in the following examples.

Example 5: Catalytic Assembly: Mixture of Iron Powders and of Catalyst

The catalyst bed consists of nickel particles on cerium oxide: Ni: 0.09 g/$CeO_2$: 0.91 g, mixed with 2 g of iron powder. The gas flow is downward, at a constant flow rate of 20 mL/min of $H_2$ and 5 mL/min of $CO_2$.

Figure 4:
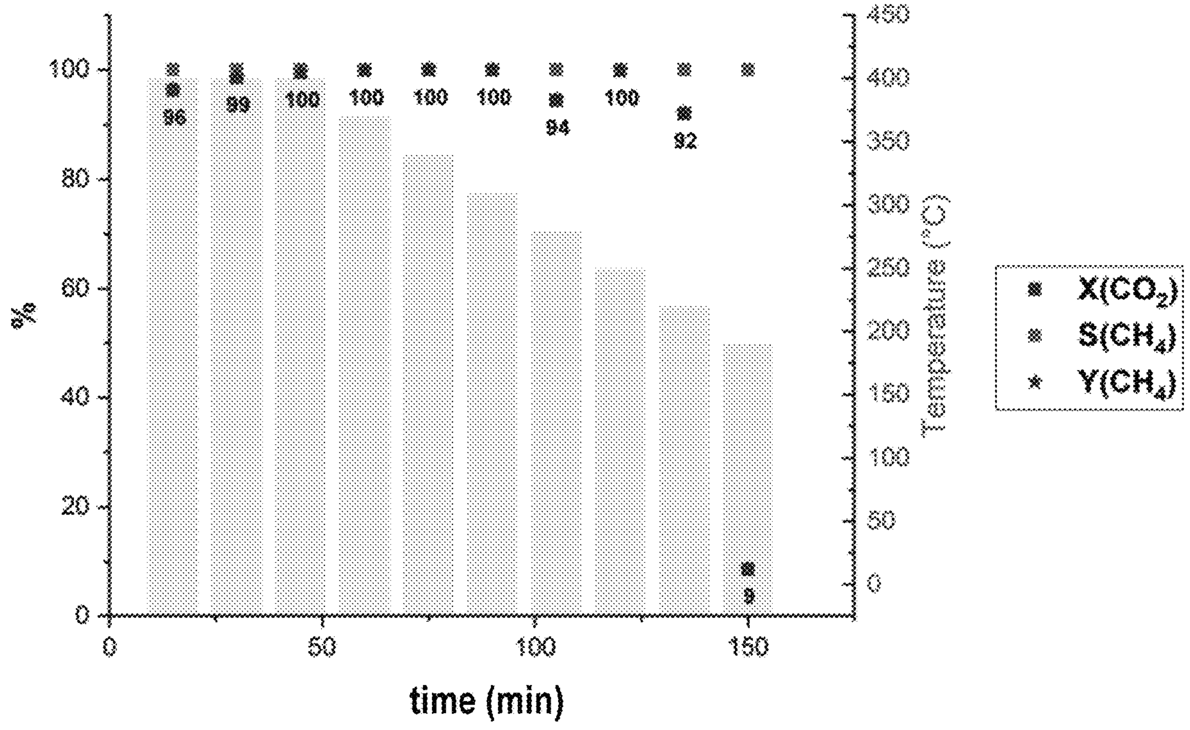
FIG. 4 is a histogram showing the conversion rates (in %) of $CO_2$ and of $CH_4$ and also the selectivity as a function of time and temperature for a methanation reaction in downward flow in the presence of a mixture of iron powder and $Ni/CeO_2$.

The results of the conversion rates of $CO_2$ and of $CH_4$ are presented in FIG. 4. This assembly of powders (iron powder+Ni/$CeO_2$) makes it possible to obtain very satisfactory yields ($Y(CH_4)$), reaching 100% at temperatures of 300-350° C.

Example 6: Catalytic Assembly: Mixture of Steel Wool and Ni/$CeO_2$ Catalyst

The catalyst bed consists of nickel particles deposited on cerium oxide: Ni: 0.09 g/$CeO_2$: 0.91 g and of 0.35 g of superfine steel wool. The gas flow is downward, at a constant flow rate of 20 mL/min of $H_2$ and 5 mL/min of $CO_2$.

Figure 5:
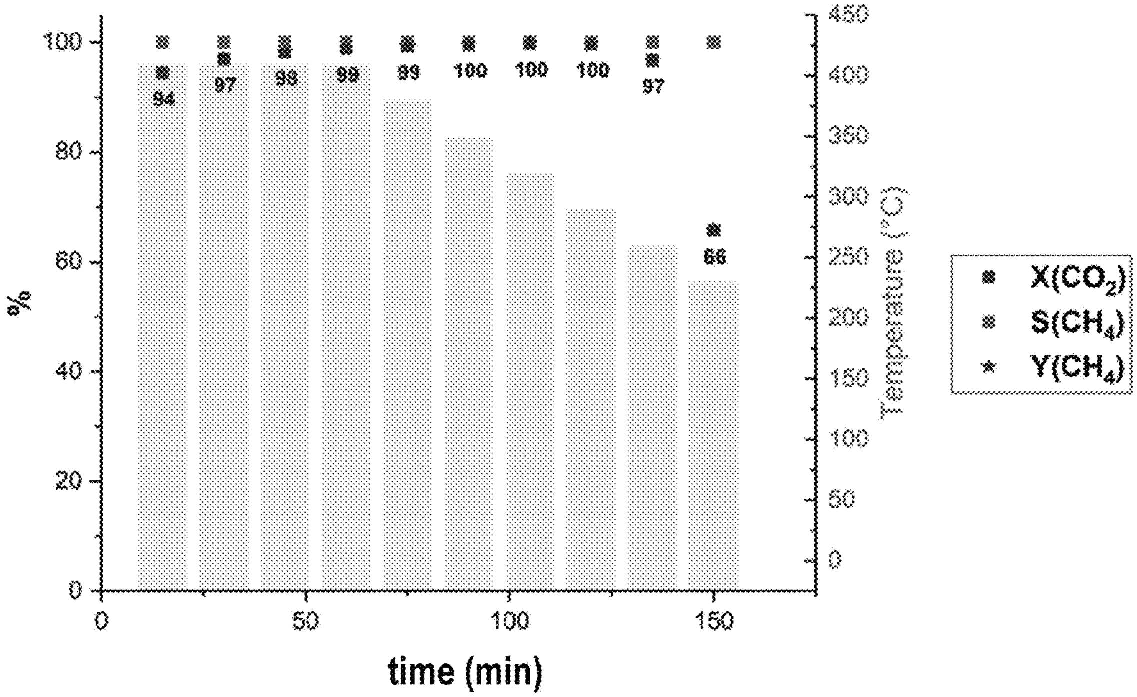
FIG. 5 is a histogram showing the conversion rates (in %) of $CO_2$ and of $CH_4$ and also the selectivity as a function of time and temperature for a methanation reaction in downward flow in the presence of a mixture of steel wool and $Ni/CeO_2$.

The results of the conversion rates of $CO_2$ and of $CH_4$ are presented in FIG. 5. This steel wool+Ni/$CeO_2$ assembly also makes it possible to obtain very satisfactory yields ($Y(CH_4)$), reaching 100% at temperatures of 300-350° C.

Example 7: Catalytic Assembly: Ni Deposited on Steel Wool

The catalyst bed consists of nickel particles: Ni: 0.03 g deposited on 2.27 g of superfine steel wool. The gas flow is downward, at a constant flow rate of 20 mL/min of $H_2$ and 5 mL/min of $CO_2$.

Figure 6:
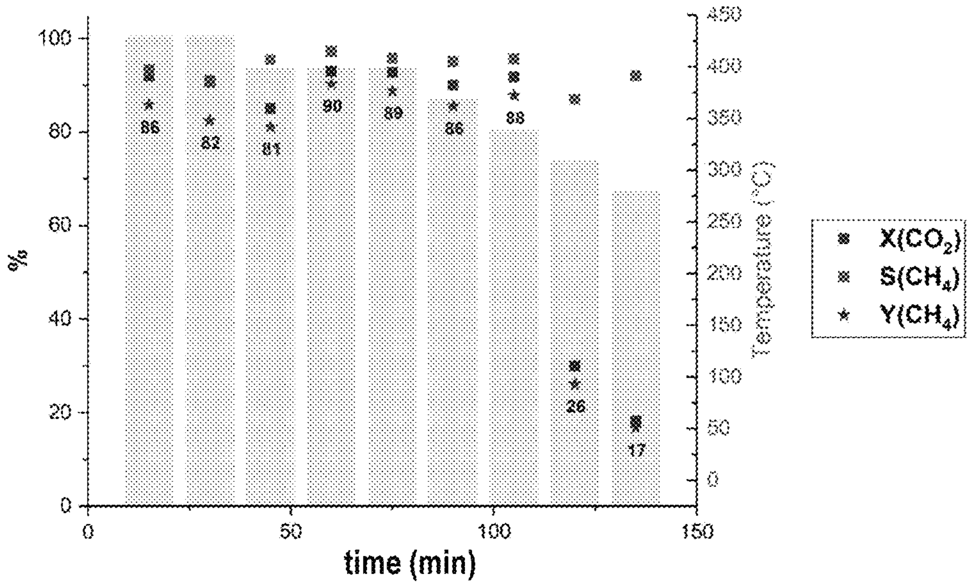
FIG. 6 is a histogram showing the conversion rates (in %) of $CO_2$ and of $CH_4$ and also the selectivity as a function of time and temperature for a methanation reaction in downward flow in the presence of nickel on steel wool.

The results of the conversion rates of $CO_2$ and of $CH_4$ are presented in FIG. 6. The maximum yield ($Y(CH_4)$) is 90% at 400° C. This result is very encouraging, knowing that this system is simpler to implement.

Example 8: Energy Efficiency

The energy efficiency calculations of the preceding three examples (examples 5, 6 and 7) grouped together in FIG. 7 show that it is necessary to provide less energy to the catalytic assembly comprising the steel wool than to the catalytic assembly comprising the iron powder in order to reach the same temperature. This difference between powder and wool is observed particularly with the steel wool+Ni/$CeO_2$ system. The energy efficiency of the steel wool+Ni catalytic assembly is not as good since there is more wool to heat and therefore more energy to provide for a same amount of methane produced. In the example presented, it was necessary to introduce a larger amount of steel wool, since very little nickel had been deposited thereon, in order to achieve an advantageous yield (90%).

The invention claimed is:

1. A catalytic assembly for carrying out a heterogeneous catalysis reaction, comprising:

either the combination of at least one catalytic compound formed of metallic particles for catalyzing said reaction; and a ferromagnetic material in the form of micrometric particles having a particle size of between 1 μm and 1000 μm and of wires based on iron or on an iron alloy having a wire diameter of between 1 μm and 1 mm, or the combination of at least one catalytic compound formed of metallic particles and capable of catalyzing said reaction; and a ferromagnetic material in the form of wires based on iron or on an iron alloy having a wire diameter of between 1 μm and 1 mm, wherein the ferromagnetic material of either of said combinations, that is in the form of wires, comprises steel wool in the form of an entanglement of wires, and wherein said ferromagnetic material being capable of being heated by magnetic induction by means of a field inductor, wherein said steel wool is provided in an amount, and of dimensions, sufficient such that it requires less energy to be provided to the catalytic assembly comprising the steel wool for carrying out the heterogeneous catalysis reaction, than an amount of energy needed to be provided to the catalytic assembly comprising the iron powder in order to reach a same temperature of reaction.

2. The catalytic assembly as claimed in claim 1, wherein said catalytic assembly is in the form of a powder comprising a mixture of at least one catalytic compound in particulate form with micrometric particles of the ferromagnetic material.

3. The catalytic assembly as claimed in claim 1, wherein the micrometric particles of the ferromagnetic material have a particle size of between 1 μm and 100 μm.

4. The catalytic assembly as claimed in claim 1, wherein said catalytic compound is formed of metallic catalyst particles which are positioned at the surface of an oxide forming a support for the catalyst, wherein said oxide is an oxide selected from the group consisting of: silicon, aluminum, titanium, zirconium, and cerium, constituting a catalyst-oxide compound.

5. The catalytic assembly as claimed in claim 1, wherein the catalytic compound comprises metallic catalyst particles which are positioned at the surface of the ferromagnetic material that is in the form of wires.

6. The catalytic assembly as claimed in claim 5, wherein the steel wool contains wires based on iron or on an iron alloy having a wire diameter of between 20 μm and 500 μm.

7. The catalytic assembly as claimed in claim 1, wherein the ferromagnetic material is composed of steel wool defined as "superfine", comprising an entanglement of wires composed of at least 90 wt % iron, and of which the diameter of the wires is between 50 μm and 100 μm.

8. The catalytic assembly as claimed in claim 4, wherein the metallic catalyst particles of the catalytic compound are selected from the group consisting of manganese, iron, nickel, cobalt, copper, zinc, ruthenium, rhodium, palladium, iridium, platinum, tin, and an alloy comprising one or more of these metals.

9. The catalytic assembly as claimed in claim 8, wherein the metallic catalyst particles of the catalytic compound are nickel or ruthenium particles.

10. The catalytic assembly as claimed in claim 1, wherein said catalytic assembly is configured to implement a heterogeneous catalysis reaction including the contacting, in a reactor, of at least one reactant with said catalytic assembly and the heating of said ferromagnetic material by magnetic induction by means of a field inductor external to the reactor, so as to catalyze said reaction.

11. The catalytic assembly as claimed in claim 10, wherein the heterogeneous catalysis reaction is a hydrocarbon synthesis reaction.

12. The catalytic assembly as claimed in claim 10, wherein the heterogeneous catalysis reaction is a hydrogenation reaction of a carbon oxide in the gaseous state.

13. The catalytic assembly as claimed in either of claim 3, wherein the micrometric particles of the ferromagnetic material have a particle size of between 1 μm and 50 μm.

14. The catalytic assembly as claimed in either of claim 3, wherein the micrometric particles of the ferromagnetic material have a particle size of between 1 μm and 10 μm.

15. The catalytic assembly as claimed in claim 6, wherein the steel wool contains wires based on iron or on an iron alloy having a wire diameter of between 50 μm and 200 μm.

16. The catalytic assembly as claimed in claim 1, wherein the ferromagnetic material comprises at least 50 wt % iron.

17. The catalytic assembly as claimed in claim 1, wherein the ferromagnetic material comprises at least 80 wt % iron.

18. The catalytic assembly as claimed in claim 1, wherein the heterogeneous catalysis reaction is a methanation reaction starting from carbon dioxide and dihydrogen.

19. The catalytic assembly as claimed in claim 1, wherein the steel wool contains wires based on iron or on an iron alloy and having a wire diameter of between 10 μm and 1 mm.

20. The catalytic assembly as claimed in claim 1, wherein the steel wool contains wires based on iron or on an iron alloy and having a wire diameter of between 50 μm and 200 μm.

* * * * *